United States Patent [19]

Vishwakarma et al.

[11] Patent Number: 5,739,348

[45] Date of Patent: Apr. 14, 1998

[54] METHOD OF SYNTHESIZING TERT-AMIDO-SUBSTITUTED 2-(2'-HYDROXYPHENYL) BENZOTRIAZOLE COMPOUNDS IN A ONE-STEP PROCESS

[75] Inventors: Lal Chand Vishwakarma, Rochester; Victor LaVonne Mylroie, Fairport, both of N.Y.

[73] Assignee: Eastman Kodak Company, Rochester, N.Y.

[21] Appl. No.: 735,544

[22] Filed: Oct. 23, 1996

[51] Int. Cl.⁶ .................................................. C07D 249/20
[52] U.S. Cl. ........................................ 548/260; 548/259
[58] Field of Search ............................. 548/259, 260

[56] References Cited

U.S. PATENT DOCUMENTS

| | | | |
|---|---|---|---|
| 3,272,891 | 9/1966 | Peter et al. | 260/895 |
| 3,399,173 | 8/1968 | Heller et al. | 260/47 |
| 4,041,044 | 8/1977 | White | 260/308 |
| 4,141,903 | 2/1979 | Adler | 260/308 |
| 4,224,451 | 9/1980 | Roberts et al. | 548/260 |
| 4,719,248 | 1/1988 | Bambury et al. | 523/108 |
| 4,780,541 | 10/1988 | Selmo | 548/260 |
| 4,835,284 | 5/1989 | Seino | 548/259 |
| 4,943,637 | 7/1990 | Seino et al. | 548/260 |
| 5,262,541 | 11/1993 | Moshchitsky et al. | 548/260 |
| 5,500,332 | 3/1996 | Vishwakarma et al. | 430/512 |

FOREIGN PATENT DOCUMENTS

| | | |
|---|---|---|
| 0 257 151 | 3/1988 | European Pat. Off. |
| 1324898 | of 0000 | France |
| 960141 | 6/1964 | United Kingdom |
| 981539 | 1/1965 | United Kingdom |
| 991142 | 5/1965 | United Kingdom |
| 991204 | 5/1965 | United Kingdom |
| 991320 | 5/1965 | United Kingdom |
| 991630 | 5/1965 | United Kingdom |
| 90/09369 | 8/1990 | WIPO |

*Primary Examiner*—Patricia L. Morris
*Attorney, Agent, or Firm*—Edith A. Rice

[57] ABSTRACT

A method for preparing a compound of formula (III):

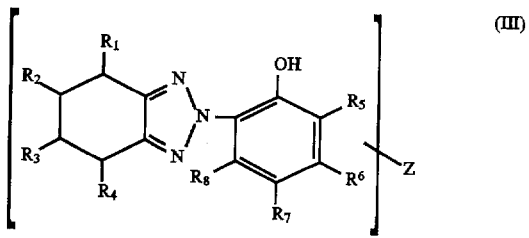

wherein:

$R_1$, $R_2$, $R_3$, $R_4$, $R_5$, $R_6$, $R_7$, $R_8$, L, Z and p are as defined in the specification;

said process preferably comprising either a noble metal catalyzed hydrogenation or a non-catalytic reductive ring closure of an azo dye compound of formula (IV):

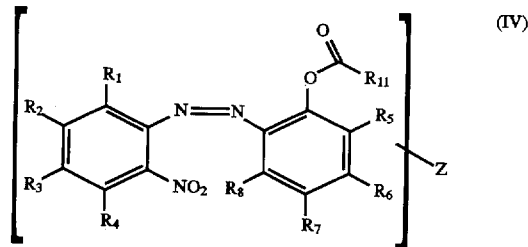

where R11 is as defined in the specification, thereby performing a reductive ring closure and selective O-deacylation in a single process step.

14 Claims, No Drawings

METHOD OF SYNTHESIZING TERT-AMIDO-SUBSTITUTED 2-(2'-HYDROXYPHENYL) BENZOTRIAZOLE COMPOUNDS IN A ONE-STEP PROCESS

FIELD OF THE INVENTION

This invention relates to a method of synthesizing tert-amido-substituted 2-(2'-hydroxyphenyl)benzotriazole compounds which are useful as ultraviolet absorbing compounds.

BACKGROUND OF THE INVENTION 2-(2'-Hydroxyphenyl)benzotriazole compounds are known in the art as ultraviolet absorbing compounds useful for paints, plastics, polymers, coatings, and protection of synthetic fibers against sunlight (e.g., see M. Dexter in "Encyclopedia of Chemical Technology" (Kirk-Othmer), 3rd Edition, Vol. 23, pp.615–627 (Wiley-Interscience, New York 1983)). U.S. Pat. Nos. 3,159,646; 3,383,241; 3,368, 916; 3,367,958; and GB 1,102,819 describe uses of such compounds for high molecular weight compounds. These are also used in design of lightfast disperse dyes (see, e.g., H. S. Freeman and J. C. Posey, Jr. in Dyes and Pigments Volume 20, pp 171–195 (1992)). For their uses in wool industry, see, Australian Patent Application No. 7152/82, dated Dec. 7, 1982, also see, I. H. Leaver, P. J. Waters, N. A. Evans, *Journal of Polymer Science, Polymer Chemistry Education*, Volume 17, page 1531 (1979). Water-soluble benzotriazole-basedW absorbing compounds, as disclosed in Japanese Kokai JP 50-121178, represented by a formula (I) such as

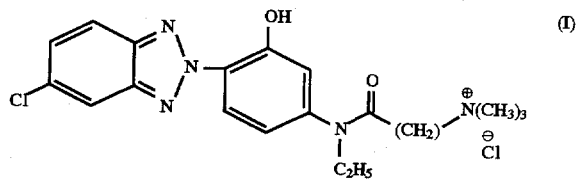

are used for preventing the sensitivity of organic compounds in various products such as cosmetics, fibers, foods etc. Such compounds are widely used by photographic industry particularly in silver halide photographic elements for protection of yellow, magenta and cyan image dyes from fading in color photographic prints. Such compounds with a 4'- or 5'-amino substituent in benzotriazole rings are known in the prior art, and are used to prepare various ultraviolet absorbing derivatives. For example, the use of such 4'- or 5'- amino substituted compounds are described in U.S. Pat. Nos. 3,272,891; 3,399,173; 4,719,248; 5,500,332; WO 9009369; FR 1,330,378; FR 1,324,898; FR 1,324,897; GB 960 141; GB 981 539; GB 991 204; GB 991 320; GB 991 142; GB 991 630; and GB 991 204 and the references described in them. 4'-tert-Amido-substituted benzotriazole(s) such as in formula (II) (also referered to herein as (XXXVI)):

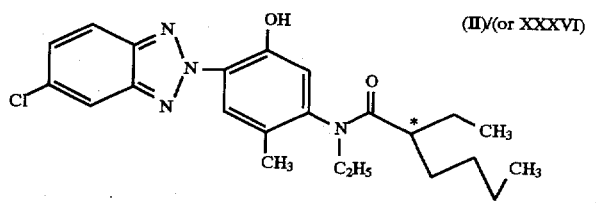

are particularly useful in silver halide imaging applications (See commonly assigned patent application Ser. No. 08/735, 543, filed concurrently herewith, Attorney Docket 74,506). Tert-amido-substituted benzotriazole compounds may find uses in many industries.

Synthetic procedures for amino substituted benzotriazoles described in aforesaid prior art involve reduction of the corresponding o-nitro azo dyes using zinc dust in presence of alkali metal hydroxides. Zinc dust has at least three-fold problems: first, it frequently causes dechlorination from the benzotriazole rings under uncontrolled reaction conditions; second, it is no longer environmentally acceptable; and third, results in relatively low yield of the desired product, e.g., in the range of about 50–60%. Moreover, zinc dust reduction frequently fails with highly functionalized o-nitro azo dyes which are used as precursors for benzotriazoles.

Other non-zinc processes, such as use of thiourea-S,S-dioxide, have been used for amino-substituted benzotriazoles and did not cause dechlorination, but the yields were low, e.g., see H. S. Freeman and J. C. Posey, Jr. in *Dyes and Pigments* Volume 20, pp 171–195 (1992) where phenolic hydroxy and and anilino amino groups of the azo dye precursor were unprotected. Some non-zinc processes are also reported in, for example, EP 0 257 151; U.S. Pat. Nos. 5,262,541; 4,780,541; 4,943,637; 4,224,451; 4,141,903; 4,041,044; and 4,835,284 but amino or amido substituents on benzotriazole rings are not reported in these references.

In commonly assigned copending application U.S. Ser. No. 60/000,663 filed on Jun. 29, 1995 a non-catalytic process is disclosed and in commonly assigned copending application U.S. Ser. No. 08/611,964, filed on Mar. 7, 1996 a catalytic hydrogenation process is disclosed, both of which provide excellent yields of benzotriazole products if the reductive ring closure is carried out with both protected phenolic and anilino groups with a suitable protecting group, followed by deprotection of both groups in the resulting benzotriazole compounds in an additional step. Moreover, deprotection of a sec-amido group or of a tert-amido group or of a carbamato group requires harsh reaction conditions. Now, because we have found that a compound of formula (II)/(or XXXVI) and other similar tert-amido-substituted benzotriazoles are photographically important (see commonly assigned application Ser. No. 08/735,543 filed concurrently herewith, Attorney Docket No. 74,506), it was desired to find an economical and environmentally acceptable process to manufacture such compounds.

SUMMARY OF THE INVENTION

Now we have discovered a one-step process (catalytic or non-catalytic) to make compounds of formula (III) and other related compounds from readily available di-protected azo dye precursor compounds of formula (IV) wherein reductive ring closure and selective O-deacylation takes place in a single step.

Accordingly, the present invention provides a method for preparing a compound of formula (III):

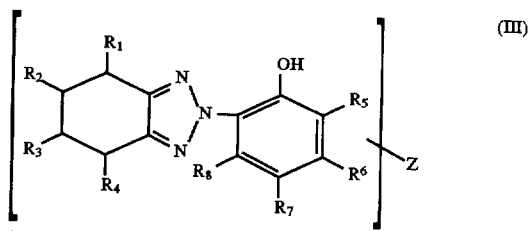

wherein:

$R_1$, $R_2$, $R_3$, $R_4$, $R_5$, $R_6$, $R_7$ and $R_8$ are independently: H; halogen; cyano; —$CO_2Y$ where Y is H or an alkyl group or aryl group; carbamoyl group; sulfoxido group; sulfonyl group; sulfonato group; sulfonamido group; alkyl group; alkoxy group; aryl group; heteroaryl group; aryloxy group; or any two or more of adjacent ones of $R_1$ through $R_4$, or $R_5$ through $R_7$ may together form an alicyclic group, or complete, together with the carbon atoms of the benzene ring to which they are attached, an aromatic group or heteroaryl group; or Z, with the proviso that at least one of $R_1$ through $R_8$ is Z; or $R_8$ is OH; where Z is a group of the formula:

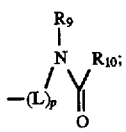

where L is a linking group; $R_9$ and $R_{10}$ are independently: a branched or unbranched alkyl or perfluoro alkyl Group which may contain one or more hetero atoms and may be substituted with one or more hydroxyl groups, and p is 0 or 1;

said process comprising ring closure of an azo dye compound of formula (IV):

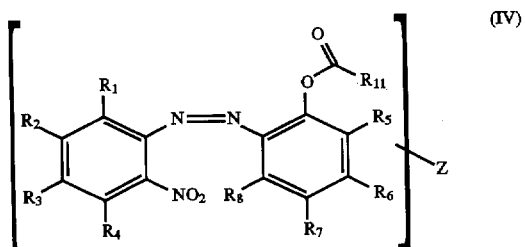

whereby the ester group —OCOR$_{11}$ is removed during the ring closure step liberating the free phenolic group, where $R_{11}$ is a branched or unbranched alkyl or perfluoro alkyl group which may contain one or more hetero atoms and may be substituted with one or more hydroxyl groups, and may be the same as or different from $R_{10}$.

The process is a noble metal catalyzed hydrogenation or a non-catalytic reductive ring closure of the azo dye of formula (IV).

Advantageous Effect of the Invention

The process of this invention can be used to accomplish reductive ring closure and selective O-deacylation in a single step leading to the desired compounds of formula (III). Further, the process provides high yields of the desired benzotriazole compound without significant formation of undesired side products. In the event the o-nitrophenyl azo dye compound is substituted with a halogen atom, no dehalogenation occurs as opposed to observed in zinc dust reduction process.

Embodiments of the Invention

In preferred embodiments of the invention, $R_1$, $R_2$, $R_3$, $R_4$, $R_5$, $R_6$, $R_7$ and $R_8$ are, independently: H; halogen; cyano; —CO$_2$Y where Y is H or a 1 to 12 (preferably 1 to 6) carbon atom alkyl or 6 to 20 (preferably 6 to 10) carbon atom aryl group; 1 to 12 (preferably 2 to 9) carbon atom carbamoyl group; 0 to 12 (preferably 2 to 4) carbon atom sulfoxido group; 0 to 12 (preferably 1 to 10) carbon atom sulfonyl group; 0 to 12 (preferably 1 to 10) carbon atom sulfonato group; 0 to 12 (preferably 1 to 10) carbon atom sulfonamido group; 1 to 18 (preferably 1 to 10) carbon atom alkyl group; 1 to 18 (preferably 1 to 10) carbon atom alkoxy group; 6 to 20 (preferably 6 to 10) carbon atom aryl group; 5 to 20 (preferably 5 to 10) atom heteroaryl group having 1 to 4 (preferably 1 to 3) hetero atoms selected from O, N or S; 6 to 20 (preferably 6 to 10) carbon atom aryloxy group; or any two or more of adjacent ones of $R_1$ through $R_4$, or $R_5$ through $R_7$ may together form a 1 to 10 carbon atom alicyclic group, or complete, together with the carbon atoms of the benzene ring to which they are attached, a 6 to 20 (preferably 6 to 10) carbon atom aromatic group or a 5 to 20 (preferably 5 to 10) atom heteroaryl group having 1 to 4 (preferably 1 to 3) hetero atoms selected from O, N or S; or Z as defined above, or $R_8$ is OH.

L is a linking group which may be a hetero atom such as O, S, N, P and the like or a substituted or unsubstituted alkylene group or cycloalkyl group with or without intervening hetero atoms or an aryl or a heteroaryl group and may be linked to a benzene ring to which it is attached through a heteroatom, and p is 0–1.

$R_9$, $R_{10}$ and $R_{11}$ may be 1–18 carbon atom branched or unbranched, preferably including one or more asymmetric carbon(s), alkyl or perfluoro alkyl group with or without intervening hetero atoms.

The starting compounds of the formula (V), are derived from unprotected azo dyes of formula (IV),

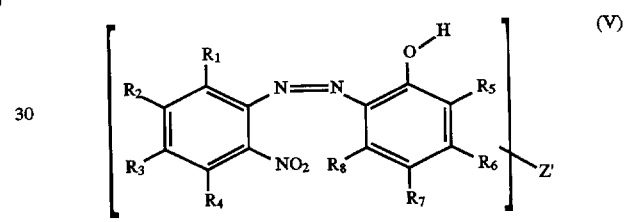

wherein Z' is a group of the formula:

wherein $R_9$, L and p are as defined above, can be made following analogous procedures from references cited above, the disclosures of which are incorporated herein by reference. They can be prepared, for example, by diazotization of an o-nitroaniline of the formula

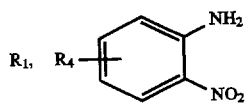

and coupling of the resulting diazonium salt onto a phenol of the formula

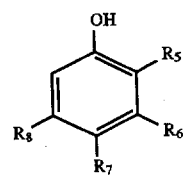

wherein, $R_1$ through $R_7$ are as previously defined, while any one of $R_1$ through $R_7$ may be

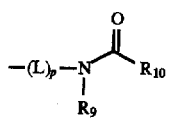

depending on where the point of attachment is desired, and $R_8$–$R_{10}$ are as previously defined. Formula (V) could be advantageously converted to compounds of formula (IV) by reacting it with the corresponding acid chloride $R_{10}COCl$ or corresponding acid anhydride in acetone/dimethylformamide solvent mixture in presence of triethylamine base and dimethylaminopyridine as a catalyst.

While not being limited by the present description, it is believed that the protection of OH and $NHR_9$ groups as described above (such that there are no free H on them), assists in providing a clean and effective ring closure to benzotriazoles by preventing formation of the imino forms. Reductive ring closure of protected azo dyes may then easily be accomplished by either commonly used reducing agents known in the art, for example, thiourea-S,S-dioxide in presence of alkali metal hydroxides or by noble metal catalyzed pressure hydrogenation. Thus, the use of traditionally used zinc dust, which may be environmentally unacceptable, can be eliminated. Reductive ring closure and selective O-deacylation of the ester group are accomplished in a single step which is an important aspect of this invention.

In the above formula (III), when reference is made to adjacent ones of $R_1$ through $R_7$, this means that they are attached to carbon atoms on the benzene or 2'-hydroxyphenyl rings shown, which carbon atoms are bonded to one another, usually with 1–10 intervening C, O, S or P atoms. Then the point of attachment of group L may be at any carbon or nitrogen atom of the fused outer ring system. It is also preferred that $R_3$ is F, Cl, Br, cyano, carboxy, carbalkoxy, 1 to 18 (preferably 1 to 8) carbon atom alkoxy group, or 0 to 12 (preferably 1 to 10) carbon atom sulfonyl Group; $R_8$ is H or OH; $R_5$ and $R_6$ are independently a 1 to 12 (preferably 1 to 8) carbon atom alkyl or H; and $R_1$ and $R_2$ are independently H, Cl or a 1 to 18 (preferably 1 to 8) carbon atom alkoxy group.

When $R_8$ in (III) is OH, that OH is also protected on formula (IV) prior to the ring closure step, to form —O(COR$_{10}$), wherein COR$_{10}$ group is removed during the ring closure step.

The method of the present invention may also encompass the formation of the compound of formula (V) by diazotizing the compound of formula (VI) with an aqueous acidic nitrite salt to obtain the compound of formula (VII), and coupling the compound of formula (VII) with the compound of formula (VIII) to obtain the compound of formula (V), as shown below in Scheme 1.

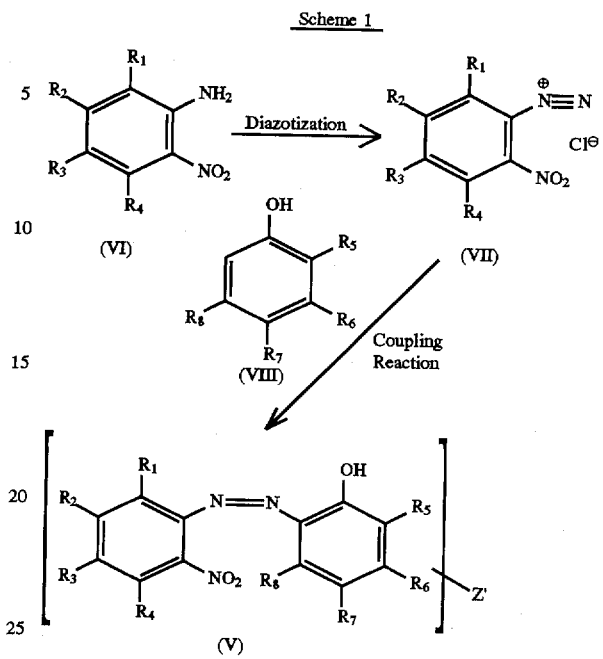

Scheme 1 wherein $R_1$ to $R_8$, Z', L and p are as defined above for formulas (III) and (IV) and L may be attached to either of the rings replacing any of $R_1$ through $R_8$. Therefore, by definition L may be part of (VI) or (VIII).

The present invention can use the diazotization step to prepare unprotected compounds of formula (V) in yields from 87 to 99% by diazotizing 2-nitroanilines (VI) and condensing with corresponding phenol derivative (VIII) following the general procedure known in the art, for example: U.S. Pat. Nos. 3,072,585; 3,159,646; 3,813,255; and 4,780,541; pending U.S. patent application Ser. No. 08/313,492; FR 1,330,378; FR 1,324,898; FR 1,324,897; GB 991 204; GB 991 320; GB 991 142; GB 991 630; and GB 991 204 and the references described in them. Those references and all other references cited in the present application, are incorporated herein in their entirety by reference.

Protection of OH and $NHR_9$ groups of compounds of formula (V), as discussed above can be achieved using various acylating reagents, such as $R_{10}COCl$ or $R_{11}COCl$ or their corresponding acid anhydride. It will be appreciated that the exact reaction conditions which may be used will depend on the acylating reagent being used.

In embodiments of the invention in which $R_{10}$ is not the same as $R_{11}$, protection of OH and $NHR_9$ groups takes two steps. In particularly preferred embodiments, $R_{10}$ and $R_{11}$ are the same and are preferably 1–18 carbon atoms branched (including asymmetric carbon atoms) or unbranched alkyl groups, such as methyl, ethyl, propyl, sec-butyl, octyl, 2-ethylhexyl and aryl groups and the like, e.g., $(CH_3CO)_2O$; $CH_3COCl$; n-$C_7H_{15}COCl$;

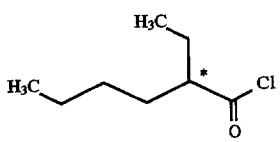

As to the ring closure step, this is preferably accomplished by reacting the protected compound of formula (IV) with a reducing agent selected from a thiourea-S,S-dioxide and a dithionite salt (such as an alkali metal salt, for example, sodium or potassium dithionite) in a basic aqueous solution. The aqueous solution is preferably an alcoholic aqueous solution, and the reaction temperature may be maintained at about 60° to about 80° C. for about 2 to 3 hours. The alcohols may be selected, for example, from ethanol, methanol, and isopropanol. The solution may, for example, be between 1 to 6 N hydroxide ion. A preferred solution is 4N sodium hydroxide in a 50/50 (by volume) methanol/water solution.

As to the ring closure step, this can be accomplished by various known methods. These include catalytic hydrogenation of the protected compound of formula (IV). Catalytic hydrogenation is usually accomplished with high pressure (for example, 1–20 atmospheres) hydrogenation in the presence of a catalyst such as palladium-charcoal or platinum, or a combination of platinum and palladium in presence of t-butylamine/or ammonium hydroxide and hypophosphorus acid as described in commonly assigned copending application Ser. No. 08/611,964 filed on Mar. 07, 1996. Another ring closure step uses a suitable hydrogen donor, such as formate salt (for example, an alkali metal salt such as sodium or potassium formate, or ammonium formate) in the presence of a catalyst (such as a palladium-charcoal catalyst). Ring closure can also be accomplished using the conventional zinc reduction method such as described in U.S. Pat. No. 3,072,585. Use of the zinc dust method still gives better results than when an unprotected azo dye compound is used. However, the use of zinc is considered less desirable due to potential adverse environmental impact from zinc use.

The deprotection step of the ester group in formula (IV) occurs during the reductive ring closure step. Protection of the phenolic OH group as an ester group, as in formula (IV), appears necessary for clean and efficient ring closure to afford compounds of this invention represented by formula (III). Any other alcoholic OH group(s) present in L or in $R_9$ groups may also get protected to esters, although their protection is not necessary for effective ring closure. Specifically, the foregoing $OCOR_{10}$ group gets hydrolyzed to free phenolic group while tert-amido group containing the same acyl group $COR_{10}$ remains intact during ring closure using thiourea-S,S-dioxide or a dithionite salt or noble metal catalyzed high pressure hydrogenation. Ester groups derived from alcoholic OH substituents in L or $R_9$ may also get deprotected to alcoholic OH group. Free alcoholic group, if present in compounds of formula (III), may further be functionalized for various uses.

It is preferred that all of the steps of the synthesis of the present invention, are performed without isolating products (other than the final product of compound (III). By "not isolating" in this context is meant that solvents or other volatile compounds may be removed, but non-volatile compounds are not removed and intermediates are not isolated.

The nitroanilines which may be used for diazotization include, but are not limited to, 2-nitroaniline, 6-methoxy-2-nitroaniline, 4-methoxy-2-nitroaniline, 4,5-dimethoxy-2-nitroaniline, 4,5-dichloro-2-nitroaniline, 4-chloro-2-nitroaniline, 4-(2-ethylhexanoyl)amino-2-nitroaniline, 4-acetyl amino-2-nitroaniline, 4-(3-hydroxypropanoyl) amino-2-nitroaniline, 4-fluoro-2-nitroaniline, 4-bromo-2-nitroaniline, 4,5-dichloro-2-nitroaniline, 4-cyano-2-nitroaniline, 4-carboxy-2-nitroaniline and the like.

The phenols which can be used as coupling components include, but are not limited to, 3-ethylaminophenol, 3-ethylamino-5-hydroxyphenol, 3-methylamino-4-methylphenol, 3-(2-N-methylamino) ethylphenol, 3-(2-hydroxyethyl)aminophenol, 3-(2-carboxyethyl) aminophenol, 3-trifluoromethylaminophenol, 3-pentafluoroethylaminophenol, and the like.

Illustrative examples of 2-nitroazobenzenes of formula (V), represented by formula (IX) and (X), are included in Tables 1 & 2, but are not limiting in scope of this invention.

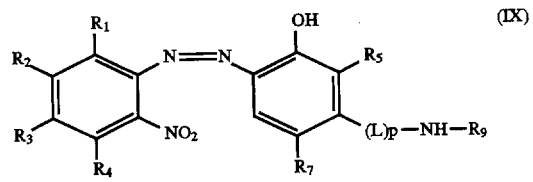

TABLE 1

| S. No | $R_1$ | $R_2$ | $R_3$ | $R_4$ | $R_5$ | L | $R_7$ | P | $R_9$ |
|---|---|---|---|---|---|---|---|---|---|
| 1 | H | H | H | H | H | Zero | H | Zero | $CH_3$, $C_2H_5$, $CF_3$, $C_2F_5$, $CH_2CH_2OH$ |
| 2 | H | H | $CH_3$ | H | H | Zero | H | Zero | $CH_3$, $C_2H_5$, $CF_3$, $C_2F_5$, $CH_2CH_2OH$ |
| 3 | H | H | Cl or F | H | H | Zero | $CH_3$ | Zero | $CH_3$, $C_2H_5$, $CF_3$, $C_2F_5$, $CH_2CH_2OH$ |
| 4 | H | H | Cl or F | H | H | Zero | H | Zero | $CH_3$, $C_2H_5$, $CF_3$, $C_2F_5$, $CH_2CH_2OH$ |
| 5 | H | H | $CH_3O$ | H | H | Zero | $CH_3$ | Zero | $CH_3$, $C_2H_5$, $CF_3$, $C_2F_5$, $CH_2CH_2OH$ |
| 6 | H | $CH_3O$ | $CH_3O$ | H | H | Zero | $CH_3$ | Zero | $CH_3$, $C_2H_5$, $CF_3$, $C_2F_5$, $CH_2CH_2OH$ |
| 7 | H | H | H or Cl | H | H | $OCH_2CH_2$ | $CH_3$ | 1 | $CH_3$, $C_2H_5$, $CF_3$, $C_2F_5$, $CH_2CH_2OH$ |
| 8 | H | H | Cl | H | H | $(OCH_2CH_2)_2$ | H | 1 | $CH_3$, $C_2H_5$, $CF_3$, $C_2F_5$, $CH_2CH_2OH$ |

TABLE 1-continued

| S. No | $R_1$ | $R_2$ | $R_3$ | $R_4$ | $R_5$ | L | $R_7$ | P | $R_9$ |
|---|---|---|---|---|---|---|---|---|---|
| 9 | H | H | COOH | H | H | $OCH_2CH_2$ | $CH_3$ | 1 | $CH_3, C_2H_5, CF_3, C_2F_5, CH_2CH_2OH$ |
| 10 | H | H | COOH | H | H | $OCH_2CH_2$ | H | 1 | $CH_3, C_2H_5, CF_3, C_2F_5, CH_2CH_2OH$ |

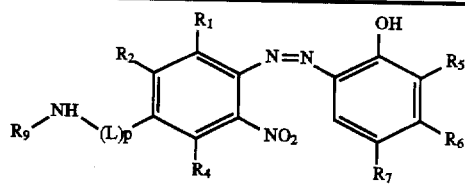

(X)

TABLE 2

| S. No | $R_1$ | $R_2$ | $R_4$ | $R_5$ | $R_6$ | L | $R_7$ | p | $R_9$ |
|---|---|---|---|---|---|---|---|---|---|
| 1 | H | H | H | H | H | Zero | H | Zero | $CH_3, C_2H_5, CF_3, C_2F_5, CH_2CH_2OH$ |
| 2 | H | H | H | H | H | Zero | H | Zero | $CH_3, C_2H_5, CF_3, C_2F_5, CH_2CH_2OH$ |
| 3 | H | H | H | H | H | Zero | $CH_3$ | Zero | $CH_3, C_2H_5, CF_3, C_2F_5, CH_2CH_2OH$ |
| 4 | H | H | H | H | H | Zero | H | Zero | $CH_3, C_2H_5, CF_3, C_2F_5, CH_2CH_2OH$ |
| 5 | H | H | H | H | H | Zero | $CH_3$ | Zero | $CH_3, C_2H_5, CF_3, C_2F_5, CH_2CH_2OH$ |
| 6 | H | $CH_3O$ | H | H | H | Zero | $CH_3$ | Zero | $CH_3, C_2H_5, CF_3, C_2F_5, CH_2CH_2OH$ |
| 7 | H | Cl | H | H | H | $OCH_2CH_2$ | $CH_3$ | 1 | $CH_3, C_2H_5, CF_3, C_2F_5, CH_2CH_2OH$ |
| 8 | H | Cl | H | H | H | $(OCH_2CH_2)_2$ | H | 1 | $CH_3, C_2H_5, CF_3, C_2F_5, CH_2CH_2OH$ |
| 9 | H | H | H | H | H | $OCH_2CH_2$ | $CH_3$ | 1 | $CH_3, C_2H_5, CF_3, C_2F_5, CH_2CH_2OH$ |
| 10 | H | H | H | H | H | $OCH_2CH_2$ | H | 1 | $CH_3, C_2H_5, CF_3, C_2F_5, CH_2CH_2OH$ |

This invention details the following general procedure of noble metal catalyzed high pressure hydrogenation of any of the o-nitroazo dye compound of formula(IV) to benzotriazole derivatives of formula (III). To a 500 mL capacity stainless steel autoclave equipped with a stirrer, external heating jacket and internal heating and cooling coils is added 0.0115 mole of o-nitroazo dye compound of formula(II), 0.25 g (dry weight) of (4% Pd/C+1% Pt/C) catalyst (obtainable from Johnson Matthey), 4 mole equivalent (with respect to the azo dye compound) of tert-butylamine, 3 mole equivalent (with respect to the azo dye compound) of 50% aqueous hypophosphorus acid and 150 mL of methanol. The autoclave is purged with nitrogen gas and then hydrogen gas and then sealed and charged with hydrogen gas to a pressure of 75 psi. The reaction is stirred at room temperature and 75 psi (recharging if necessary) for one hour. After one hour the temperature is raised to 50° C. and held at the same temperature and pressure for an additional 12 hours while recharging the hydrogen as necessary. Then the autoclave and its contents are cooled to 45°–47° C. and removed and filtered through a Celite filter aid pad to remove the catalyst. The catalyst and the residue on the filter pad are further washed with some methanol for complete recovery of the product.

The isolation of the final products from the reaction medium is carried out by conventional methods known to one skilled in the art. It varies, depending on the type of solvent used. The organic solvents are removed completely on a rotary evaporator or by a large scale distillation setup whenever recovery of easily distillable organic amine is important for recycling The left-over residue is diluted with appropriate volume of brine (aqueous sodium chloride solution) and acidified with hydrochloric acid until Congo Red indicator paper turns blue. The precipitate (if the product is solid) is collected by filtration, washed with cold water and recrystallized from a suitable solvent. If the product is liquid or very low-melting solid, it generally oils out which is extracted with water-immiscible organic solvent such as toluene, or dichloromethane or ethyl acetate or ethyl ether. The organic layer is washed with brine and cold water, then is dried over anhydrous sodium sulfate which is removed by filtration. The crude viscous product is purified by distillation under high vacuum or by silica gel flash column chromatography eluting with mixture of heptane/ethyl acetate solvents or other solvents of comparable polarity.

The process according to the invention opens up an industrially particularly favorable and economical route for the preparation of benzotriazole derivatives of formula(III) in high purity and superior yields.

The examples which follow illustrate the process according to the invention in more detail. Therein and also in the remaining description and patent claims, percentages are by weight, unless stated otherwise.

The following examples illustrate the acylation of unprotected azo dyes of formula (V).

EXAMPLE 1

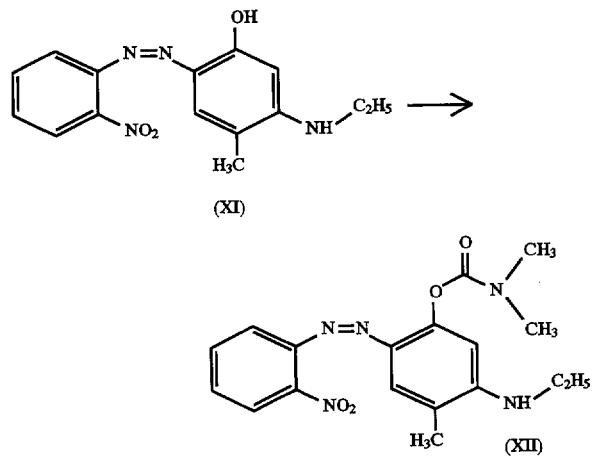

The azo dye (XI) was made following the procedure described in Scheme 1. A 5-Liter capacity 3-necked round-bottom flask was equipped on a heating mantle with a mechanical stirrer and a cold-water condenser. The flask was charged with 370.0 g (1.2321 mole) of azo dye (XI), 2,500 mL of acetone, 304.75 g (2.834 mole, 261 mL) of dimethylcarbamyl chloride, 286.2 g (2,834 mole, 394.3 mL) triethylamine, and 19.0 g (0.1555 mole, 12.6% equivalent) of dimethylaminopyridine while stirring the content of the flask. After 2 hours, 25 g more of dimethylaminopyridine and 265 mL of dimethylcarbamyl chloride and 395 mL of triethylamine were added. The reaction mixture was refluxed for 16 hours, cooled to room temperature and poured into 10 liters of mechanically stirred ice-salt-water mixture. It was allowed to settle for 40 hours at room temperature. It was filtered on a Buchner funnel, washed with cold water (3×500 mL) and air-dried. Yield, 371.4 g (81%). Its FD-MS showed peak at m/e 371 (M$^+$). Its $^1$H-NMR spectrum in CDCl$_3$ (with tetramethylsilane as internal reference) showed peaks at δ 7.8 (d, 1H, arom), 7.58 (d, and one singlet, 3H, arom), 7.4 (m, 1H, arom), 6.42 (s, 1H, arom), 4.4 (hump, 1 H, NH), 3.3 (q, 2H, N—CH$_2$—), 3.15 (s, 3H, N—CH$_3$), 3.02 (s, 3H, N—CH$_3$), 2.1 (s, 3H, CH$_3$—Ar), and 1.3 (t, 3H, CH$_2$—C̲H̲$_3$). Its retention time in HPLC was 17.23 min, was 98.5% pure by peak area percent, showing an absorption λ$_{max}$ 450 nm. It should be noted that its phenolic group is protected as a carbamato group to show later that only an ester, not a carbamato group, can undergo deprotection during ring closure step leading to desired benzotriazoles of formula (III).

Similarly, the azo compounds (XIV) and (XVI) were also prepared:

EXAMPLE 2

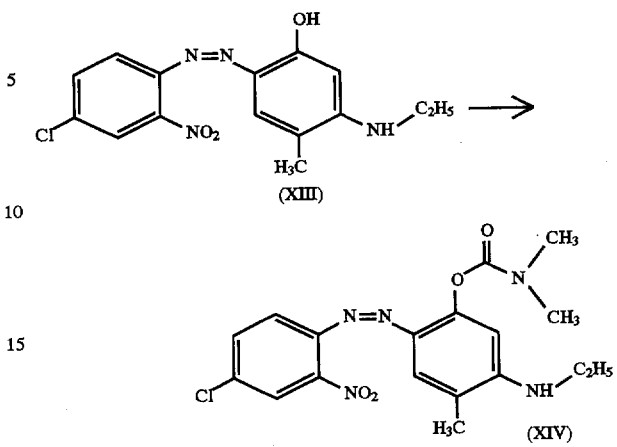

Yield, 364 g (80%). Its FD-MS showed peak at m/e 405 (M$^+$). Its $^1$H-NMR spectrum in CDCl$_3$ (with tetramethylsilane as internal reference) was consistent with its structure. Its retention time in HPLC was 18.8 min, was 99% pure by peak area percent, showing an absorption λ$_{max}$ 466 nm. It should be noted that its phenolic group is protected as a carbamato group to show later that only an ester, not a carbamato group, can undergo deprotection during ring closure step leading to desired benzotriazoles of formula (III).

EXAMPLE 3

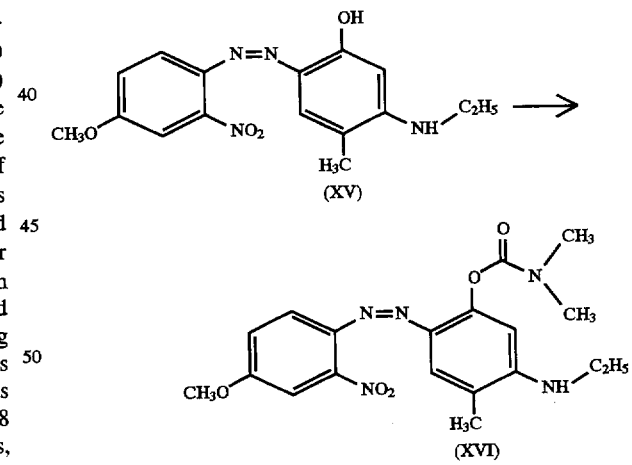

Yield, 335 g (92.7%). Its FD-MS showed peak at m/e 401 (M$^+$). Its 1H-NMR spectrum in CDCl$_3$ (with tetramethylsilane as internal reference) was consistent with its structure. Its retention time in HPLC was 17.76 min, was 99.5% pure by peak area percent, showing an absorption λ$_{max}$ 455 nm. It should be noted that its phenolic group is protected as a carbamato group to show later that only an ester, not a carbamato group, can undergo deprotection during ring closure step leading to desired benzotriazoles of formula (III).

EXAMPLE 4

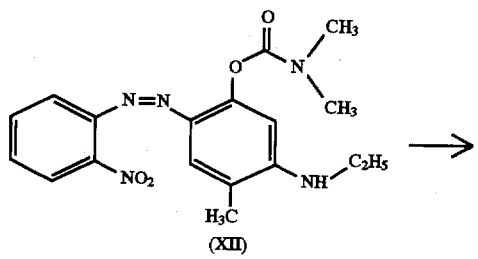

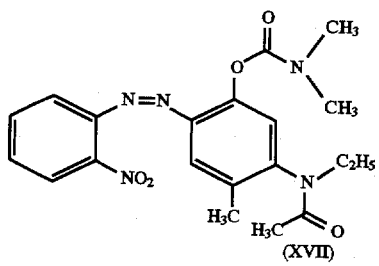

A 2-Liter capacity 4-necked round-bottom flask was equipped on a heating mantle with a mechanical stirrer and a cold-water condenser. The flask was charged with 37.1 g (0.1 mole) of azo dye (XII), 1000 mL of dimethylformamide, 3.66 g (0.03 mole, 12.6% equivalent) of dimethylaminopyridine followed by 15.7 g (0.2 mole, 14.22 mL) of acetyl chloride) at 0° C. Triethylamine (20.24 g, 27.88 mL, 0.2 mole) was added dropwise while stirring the content of the flask. After this addition was over, the reaction mixture was refluxed for three days, cooled to room temperature and poured into 10 liters of mechanically stirred ice-salt-water mixture. It was allowed to settle for 40 hours at room temperature. It was filtered on a Buchner funnel, washed with cold water (3×500 mL) and air-dried. Yield, 34.7 g (84%). Its FD-MS showed peak at m/e 413 (M⁺). It was purified by silica gel flash column chromatography. Its ¹H-NMR spectrum in CDCl₃ (with tetramethylsilane as internal reference) was consistent with the structure. Its retention time in HPLC was 14.74 min, was 98.5% pure by peak area percent, showing an absorption $\lambda_{max}$ 340 nm. It should be noted that its phenolic group is protected as a carbamato group to show later that only an ester, not a carbamato group, can undergo deprotection during ring closure step leading to desired benzotriazoles of formula (III) while tert-amido group remaining intact.

EXAMPLE 5

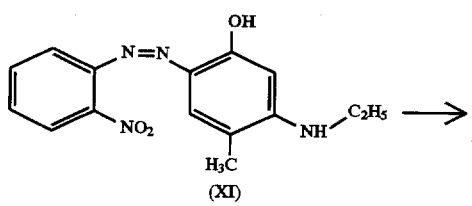

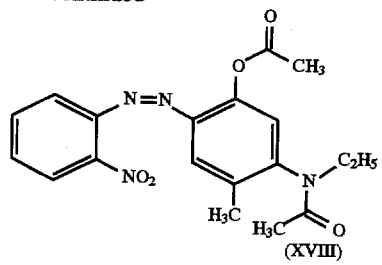

A 5-Liter capacity 3-necked round-bottom flask was equipped in a cooling bath with a mechanical stirrer and a cold-water condenser. The flask was charged with 157 g (0.52 mole) of azo dye (XI), 800 mL of dimethylformamide, 250 mL of acetone, 6.1 g (0.05 mole, 10% equivalent) of dimethylaminopyridine followed by 157 g (2.0 mole, 142 mL) of acetyl chloride) at ° C. Triethylamine (202 g, 278 mL, 2.0 mole) was added dropwise while stirring the content of the flask. After one hour of this addition, the cooling bath was replaced by a heating mantle and refluxed for one hour, cooled to room temperature and poured into 5 liters of mechanically stirred ice-salt-water mixture. It was allowed to settle for 16 hours at room temperature. It was filtered on a Buchner funnel, washed with cold water (3×500 mL) and air-dried. Yield, 164.1 g (85.4%). Its TLC in CH₂Cl₂/MeOH (9.8/0.2) showed one spot with an Rf 0.65. Its ¹H-NMR spectrum in CDCl₃ (with tetramethylsilane as internal reference) showed peaks at δ 7.9 (d, 1H, arom), 7.7 (s, 1H, arom), 7.65 (d, 1H, arom), 7.6 (d, 1H, arom), 7.5 (d, 1H, arom), 4.1 (m, 1H, proton of NCH₂), 3.3 (m, 1H, proton of NCH₂), 2.4 (s, 3H, OCOCH₃), 2.3 (s, 3H, NCOCH₃), 1.8 (s, 3H, CH₃—Ar), and 1.18 (t, 3H, CH₂CH₃). Its retention time in HPLC was 15.06 min, and showed an absorption $\lambda_{max}$ at 338 nm. Its elemental percent composition was calculated for C₁₉H₂₀N₄O₅ (M.W. 384.4): Calculated: C, 59.37; H, 5.24; N, 14.58; Found: C, 59.12; H, 5.46; N, 14.46. Its FD-MS showed a peak at m/e 384. It should be noted that its phenolic group is now protected as an ester group to show later that only an ester group can undergo deprotection during ring closure step leading to desired benzotriazoles of formula (III) while tert-amido group remaining intact.

The following examples for compounds (XIX) through (XXVI), based on general formula (IV), were made following the procedure described in Example 5. These compounds were sufficiently pure to be used in the next step (i.e., reductive ring closure and selective O-deacylation in a single experimental step) to generate compounds of general formula (III).

EXAMPLE 6

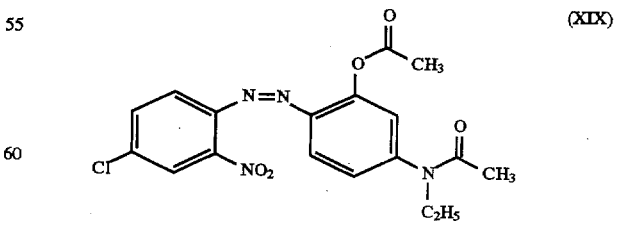

This compound was obtained as dark-orange solid. Its ¹H-NMR spectrum in DMSO-d₆ (with tetramethylsilane as internal reference) showed peaks at δ 8.35 (d, 1H, arom), 7.9 (d, 1H, arom), 7.68 (2 doublets, 2H, atom), 7.48 (s, 1H, arom), 7.4 (d, 1H, atom), 3.75 (q, 2H, CH$_2$), 2.38 (s, 3H, OCOCH$_3$), 1.95 (s, 3H, NCOCH$_3$), and 1.05 (t, 3H, CH$_3$). Its retention time in HPLC was 16.12 min, and showed an absorption λ$_{max}$ at 342 nm.

EXAMPLE 7

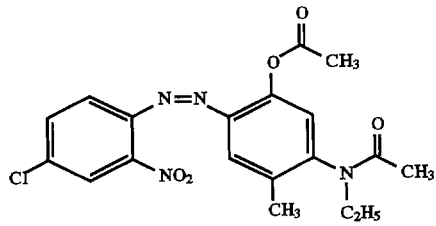

(XX)

This compound was obtained as dark-orange solid.

EXAMPLE 8

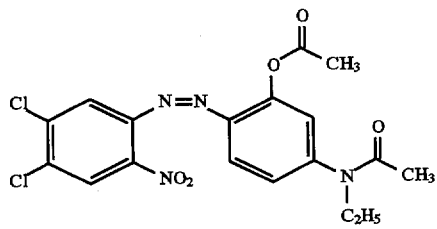

(XXI)

This compound was obtained as dark-orange solid. Its $^1$H-NMR spectrum in CDCl$_3$ (with tetramethylsilane as internal reference) showed peaks at δ 8.1 (s, 1H, arom), 7.82 (d, 1H, arom), 7.6 (s, 1H, arom), 7.18 (d, 1H, arom), 7.1 (s, 1H, atom), 3.8 (q, 2H, CH$_2$), 2.4 (s, 3H, OCOCH$_3$), 1.9 (s, 3H, NCOCH$_3$), and 1.18 (t, 3H, CH$_3$). Its retention time in HPLC was 17.23 min, and showed an absorption λ$_{max}$ at 342 nm.

EXAMPLE 9

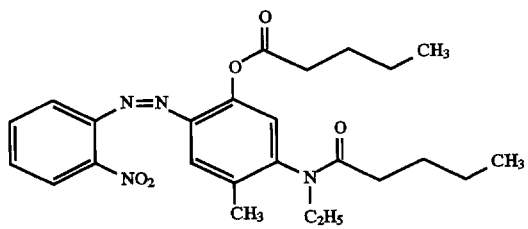

(XXII)

This compound was obtained as red-brown viscous liquid. Its FD-MS showed the desired peak at m/e 468 (M$^+$). Its TLC in CH$_2$Cl$_2$/MeOH(9.8/0.2) showed a spot at Rf 0.77.

EXAMPLE 10

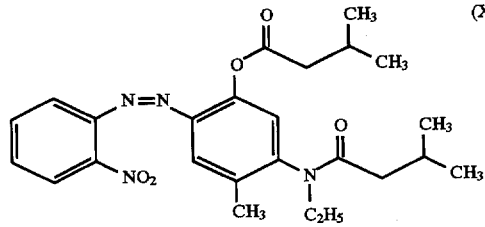

(XXIII)

This compound was obtained as red-brown viscous liquid. Its FD-MS showed the desired peak at m/e 468 (M$^+$). Its HPLC had a retention time 20.16 min showing absorption λ$_{max}$ at 338 nm.

EXAMPLE 11

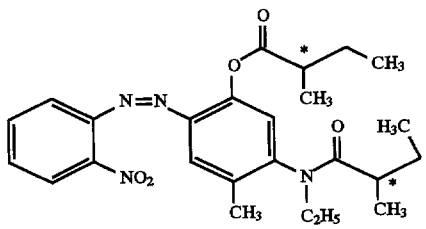

(XXIV)

This compound was obtained as red-brown viscous liquid. Its FD-MS showed the desired peak at m/e 468 (M$^+$). Its HPLC had a retention time 20.03 min showing absorption λ$_{max}$ at 338 nm.

EXAMPLE 12

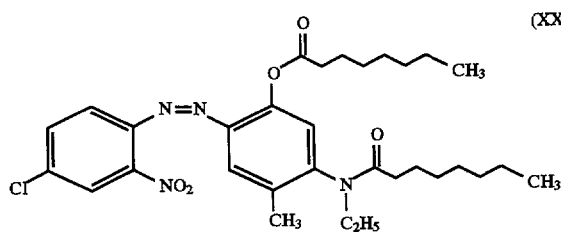

(XXV)

This compound was obtained as red-brown viscous liquid. Its FD-MS showed the desired peak at m/e 587 (M$^+$). Its HPLC had a retention time 25.3 min showing absorption λ$_{max}$ at 342 nm.

EXAMPLE 13

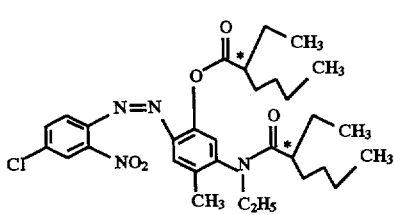

(XXVI)

This compound was obtained as red-brown viscous liquid. Its FD-MS showed the desired peak at m/e 587 (M$^+$). Its HPLC had a retention time 24.82 min showing absorption λ$_{max}$ at 342 nm.

EXAMPLE 14

This example illustrates that selective O-deacylation does not occur with non-ester protecting groups such as a carbamato group as shown below:

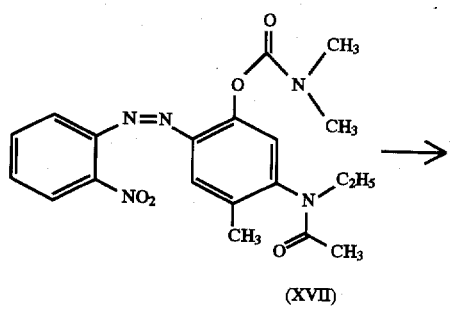

(XVII)

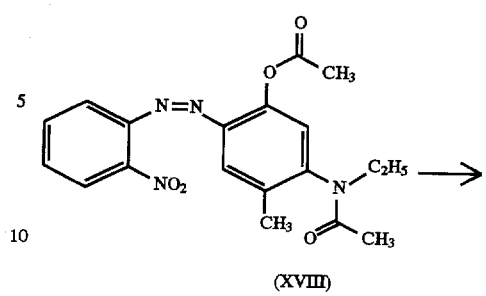

(XVIII)

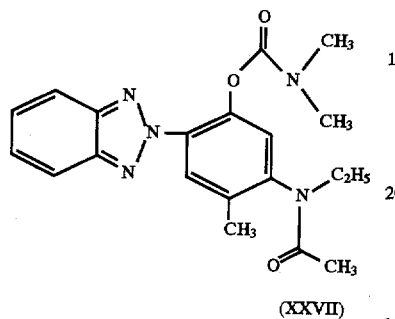

(XXVII)

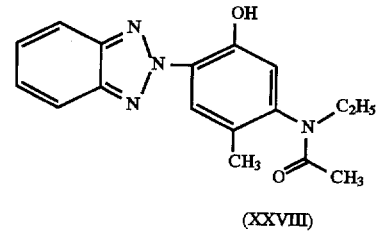

(XXVIII)

This example was carried out following previously described general procedure for noble metal catalyzed high pressure hydrogenation. To a 500 mL capacity stainless steel autoclave equipped with a stirrer, external heating jacket and internal heating and cooling coils is added 35.5 g(0.0515 mole) of o-nitroazo dye compound of formula(XVII), 0.25 g (dry weight) of (4% Pd/C +1% Pt/C) catalyst (obtainable from Johnson Matthey or some other supplier), 26.2 g of tert-butylamine (about 4 mole equivalent with respect to the azo dye compound), 35.5 g (about 3 mole equivalent with respect to the azo dye compound) of 50% aqueous hypophosphorus acid and 1100 mL of methanol. The autoclave is purged with nitrogen gas and then hydrogen gas and then sealed and charged with hydrogen gas to a pressure of 75 psi. The reaction is stirred at room temperature and 75 psi (recharging if necessary) for one hour. After one hour the temperature is raised to 50° C. and held at the same temperature and pressure for an additional 12 hours while recharging the hydrogen as necessary. Then the autoclave and its contents are cooled to 45°–47° C. and removed and filtered through a Celite filter aid pad to remove the catalyst. The catalyst and the residue on the filter pad are further washed with some methanol for complete recovery of the product.

FD-MS of the resultant product (XXVII) showed a peak at m/e 381 (M+, the molecular ion) indicating that the carbamato group and the tert-amido group both remained intact during the reductive ring closure step.

EXAMPLE 15

This example illustrates selective O-deacylation from the ester group while leaving the tert-amido group intact during noble metal catalyzed reductive ring closure.

To a 500 mL capacity stainless steel autoclave equipped with a stirrer, external heating jacket and internal heating and cooling coils is added 11.52 g (0.03 mole of o-nitroazo dye compound of formula (XVIII), 0.5 g (dry weight) of (4% Pd/C+1% Pt/C) catalyst (obtainable from Johnson Matthey or some other supplier), 8.75 G (4 mole equivalent with respect to the azo dye compound) of tert-butylamine, 3 mole equivalent (with respect to the azo dye compound) of 50% aqueous hypophosphorus acid and 275 mL of methanol. The autoclave is purged with nitrogen gas and then hydrogen gas and then sealed and charged with hydrogen gas to a pressure of 75 psi. The reaction is stirred at room temperature and 75 psi (recharging if necessary) for one hour. After one hour the temperature is raised to 50° C. and held at the same temperature and pressure for an additional 12 hours while recharging the hydrogen as necessary. Then the autoclave and its contents are cooled to 45°–47° C. and removed and filtered through a Celite filter aid pad to remove the catalyst. The catalyst and the residue on the filter pad are further washed with some methanol for complete recovery of the product.

The organic solvents are removed completely on a rotary evaporator. The left-over residue is diluted with appropriate volume of brine (aqueous sodium chloride solution) and acidified with hydrochloric acid until Congo Red indicator paper turns blue. The aqueous layer was decanted off from gummy mass, diluted with 200 mL brine and extracted with 500 mL of ethyl acetate. The organic layer is washed with brine and cold water, then is dried over anhydrous sodium sulfate which is removed by filtration. The crude viscous product is purifiedby distillation under high vacuum or by silica gel flash column chromatography eluting with dichloromethane. The solvent from the eluent was removed on a rotary evaporator. Light-brown viscous liquid is obtained which solidifies. This is triturated with $CH_2Cl_2$/pentane (1 mL/50 mL), filtered, washed with pentane and air-dried. Yield, 6.0 g(64%) is obtained as off-white solid. It has m.p. 147°–148 ° C. Its $^1$H-NMR spectrum in $CDCl_3$ (with tetramethylsilane as internal reference) showed peaks at δ 11.2 (s, 1H, phenolic OH), 8.3 (s, 1H, arom), 7.95 (two merged doublets, 2H, arom), 7.5 (two merged doublets, 2H, arom), 6.98 (s, 1H, arom), 4.08 (m, 1H from N—$CH_2$), 3.3 (m, 1H from N—$CH_2$—), 2.22 (s, 3H, $CH_3$—Ar), 1.82 (s, 3H, $NCOCH_3$) and 1.18 (t, 3H, $NCH_2\underline{CH_3}$). Its retention time in HPLC was 15.5 min, was 99.5% pure by peak area percent. Its UV-Vis (in MeOH) showed $\lambda_{max}$ 336 nm, half-bandwidth 77 nm, and $\epsilon_{max}$ 1.96×10$^4$. Its elemental percent composition was calculated for $C_{17}H_{18}N_4O_3$ (M.W. 310.4): Calculated: C, 65.79; H, 5.85; N, 18.05; Found: C, 65.35; H, 5.83; N, 17.79.

EXAMPLE 16

This example further illustrates selective O-deacylation from the ester group while leaving the tert-amido group intact during noble metal catalyzed reductive ring closure.

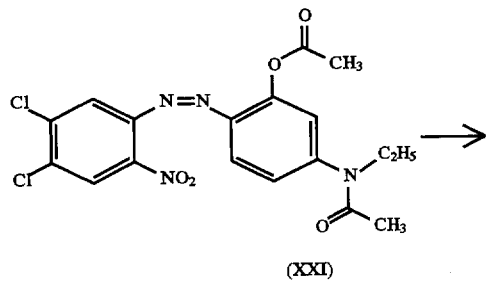

(XXI)

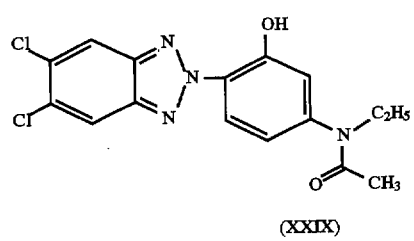

(XXIX)

This experiment was done following the procedure for Example 15. Yield (58%) is obtained as off-white solid. It has m.p. 183°–184° C. Its $^1$H-NMR spectrum in CDCl$_3$ (with tetramethylsilane as internal reference) showed peaks at δ 11.1 (s, 1H, phenolic OH), 8.4 (d, 1H, arom), 8.1 (s, 2H, arom), 7.04 (s, 1H, arom), 6.9 (d, 1H, arom), 3.82 (q, 2H, NCH$_2$CH$_3$), 1.98 (s, 3H, NCOCH$_3$) and 1.18 (t, 3H, NCH$_2$CH$_3$). Its retention time in HPLC was 17.17 min, was 99.5% pure by peak area percent. Its UV-Vis (in MeOH) showed $\lambda_{max}$ 344 nm, half-bandwidth 68 nm, and λmax 2.24×10$^4$. Its elemental percent composition was calculated for $C_{16}H_{14}Cl_2N_4O_2$ (M.W. 365.2): Calculated: C, 52.62; H, 3.86; N, 15.34; Cl, 19.41.; Found: C, 52.44; H, 3.86; N, 15.29; Cl, 19.28.

The following examples also illustrate selective O-deacylation from the ester group while leaving the tert-amido group intact even when the reductive ring closure is carried out with thiourea-S,S-dioxide (a chemical reduction process). In a general procedure, a 4-necked round-bottom flask of various capacity depending on the desired size of experiment is equipped with a mechanical stirrer, a water condenser is attached with an argon/or nitrogen gas inlet tube, a heating oil-bath is attached with a Therm-O-watch temperature controller. Typically, 0.05 mole of compound of general formula (IV) is placed in the reaction flask. This is followed by addition of 200 mL of methanol and 200 mL of 4N NaOH solution (usually 0.5–0.6 mole equivalent of sodium hydroxide while stirring the reaction mixture at room temperature. The temperature is raised to 75°–80° C. About 2.2–2.8 mole equivalent of thiourea-S,S-dioxide or sodium dthionite is added in small portions at such a rate that any frothing (if generated) should remain under control. This addition process usually takes 10–30 minutes depending on the size of experiment. The reaction mixture is stirred at the same temperature for 0.5 to 1 hour before adding the second lot, usually 1.1–1.4 mole equivalent of thiourea-S,S-dioxide or sodium dithionite. Again it is stirred at the same temperature for 0.5 to 2 hours. It is then cooled to room temperature. Methanol is removed on a rotary evaporator. The residual alkaline aqueous portion is neutralized with 0.5 to 0.6 mole equivalent (i.e. the same molar amount as sodium hydroxide) of glacial acetic acid. Preferably entire amount of solvent is removed on the rotary evaporator. About 50–200 mL of brine is added and extracted with appropriate volume of ethyl acetate. It is washed with 10% of sodium bicarbonate solution (100–300 mL) and brine (100–300 mL). The organic layer is dried over anhydrous sodium sulfate which is removed by filtration on a Buchner funnel. The organic solvent from the filtrate is removed on a rotary evaporator. The residue (if solid) is recrystallized from a suitable organic solvent. The liquid compounds were purified by silica Gel flash column chromatography eluting with heptane or heptane/ethyl acetate mixture. The yields of the products although not optimized generally are in the range 85–95%. The following examples are representative of this general procedure.

EXAMPLE 17

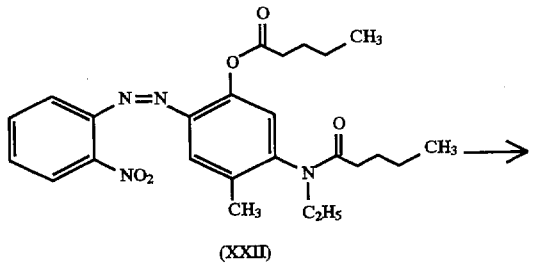

(XXII)

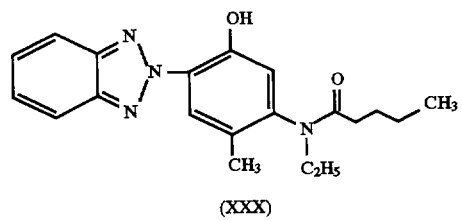

(XXX)

It has m. p. 108°–109 ° C. Its $^1$H-NMR spectrum in CDCl$_3$ (with tetramethylsilane as internal reference) showed peaks at δ 11.25 (s, 1H, phenolic OH), 8.35 (s, 1H, arom), 7.9 (m, 2H, atom), 7.5 (m, 2H, atom), 6.95 (s, 1H, arom), 4.1 (m, 1H, one proton of NCH$_2$—CH$_3$), 3.3 (m, 1H, one proton of NCH$_2$—CH$_3$), 2.25 (s, 3H, CH$_3$—Ar) and 2.08 (m, 1H, one proton of N—CO—CH$_2$—), 1.95 (m, 1H, one proton of N—CO—CH$_2$—), 1.55 (quintet, 2H, CH$_2$—CH$_2$—CH$_2$—), 1.2 (m, 5H, methyl of N-ethyl group and —CH$_2$CH$_3$ of n-butyl group), and 0.8 (t, 3H, CH$_2$—CH$_3$ of n-butyl group). Its retention time in HPLC was 18.54 min, was 99.5% pure by peak area percent. Its UV-Vis (in MeOH) showed $\lambda_{max}$ 337 nm, half-bandwidth 78 nm, and $\epsilon_{max}$ 1.96×10$^4$. Its elemental percent composition was calculated for $C_{20}H_{24}N_4O_2$ (M.W. 352.4): Calculated: C, 68.16; H, 6.86; N, 15.90; Found: C, 67.76; H, 6.71; N, 15.85.

EXAMPLE 18

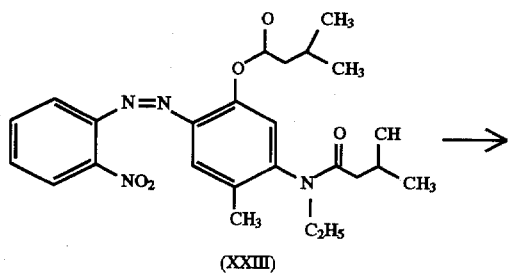

(XXIII)

→

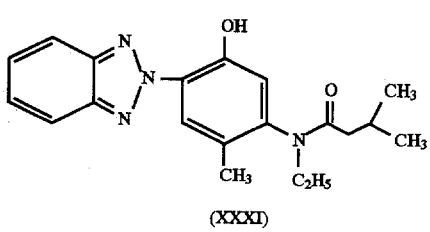

(XXXI)

It has m.p. 118°–119° C. Its $^1$H-NMR spectrum in CDCl$_3$ (with tetramethylsilane as internal reference) showed peaks at δ 11.25 (s, 1H, phenolic OH), 8.35 (s, 1H, atom), 7.95 (m, 2H, atom), 7.5 (m, 2H, arom), 6.98 (s, 1H, arom), 4.15 (m, 1H, one proton of NC$\underline{H_2}$—CH$_3$), 3.32 (m, 1H, one proton of NC$\underline{H_2}$—CH$_3$), 2.28 (s, 3H, CH$_3$—Ar), 2.20 (m, 1H, one proton of N—CO—CH$_2$—), 2.0 (two doublets, 1H, one proton of N—CO—CH$_2$—), 1.85 (two doublets, 1H, methine), 1.2 (t, 3H, NCH$_2$C$\underline{H_3}$), and 0.9 (d, 6H, gem-dimethyls). Its retention time in HPLC was 18.4 min, was 99% pure by peak area percent. Its API-mass spectrum showed m/e peak at 353 (MH$^+$). Its UV-Vis (in MeOH) showed λ$_{max}$ 336 nm, half-bandwidth 78 nm, and ε$_{max}$ 1.96×10$^4$. Its elemental percent composition was calculated for C$_{20}$H$_{24}$N$_4$O$_2$ (M.W. 352.4): Calculated: C, 68.16; H, 6.86; N, 15.90; Found: C, 68.00; H, 6.61; N, 15.50.

EXAMPLE 19

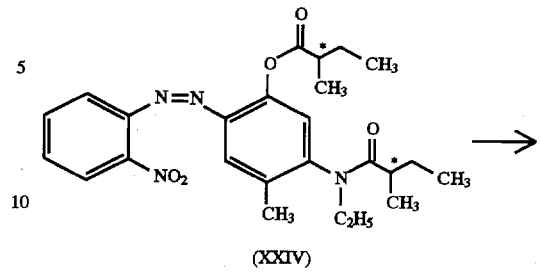

(XXIV)

→

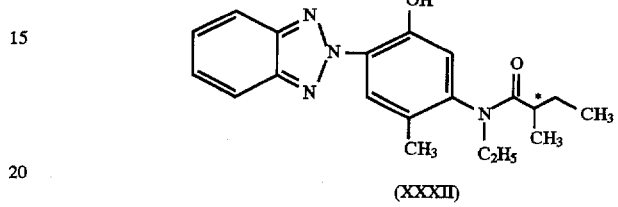

(XXXII)

This was obtained as a liquid compound which solidified at room temperature. It has m.p. 80°–82° C. Its $^1$H-NMR spectrum in CDCl$_3$ (with tetramethylsilane as internal reference) showed peaks at δ 11.22 (s, 1H, phenolic OH), 8.35 (s, 1H, arom), 7.96 (m, 2H, arom), 7.53 (m, 2H, arom), 7.0 (s, 1H, atom), 4.20 (m, 1H, one proton of N C$\underline{H_2}$—CH$_3$), 3.28 (m, 1H, one proton of NC$\underline{H_2}$—CH$_3$), 2.3 (s, 3H, CH$_3$—Ar), 2.12 (m, 1H, methine), 1.7 (m, 1H, one proton of N—C$\underline{H_2}$CH$_3$), 1.35 (m, 1H, one proton of N—C$\underline{H_2}$CH$_3$), 1.15 (m, 3H, CHC$\underline{H_3}$), and 1.02 (t, 3H, NCH$_2$C$\underline{H_3}$), and 0.85 (m, 3H, C—C$\underline{H_2}$CH$_3$). Its retention time in HPLC was 18.2 min, was 98.5% pure by peak area percent. Its API-mass spectrum showed m/e peak at 353 (MH$^+$). Its UV-Vis (in MeOH) showed λ$_{max}$ 337 nm, half-bandwidth 78 nm, and ε$_{max}$ 1.99×10$^4$. Its elemental percent composition was calculated for C$_{20}$H$_{24}$N$_4$O$_2$ (M.W. 352.4): Calculated: C, 68.16; H, 6.86; N, 15.90; Found: C, 67.81; H, 6.77; N, 15.81.

EXAMPLE 20

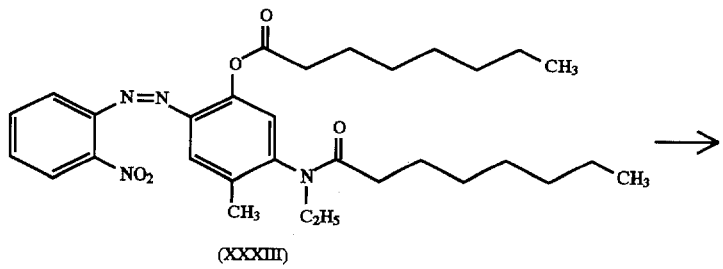

(XXXIII)

→

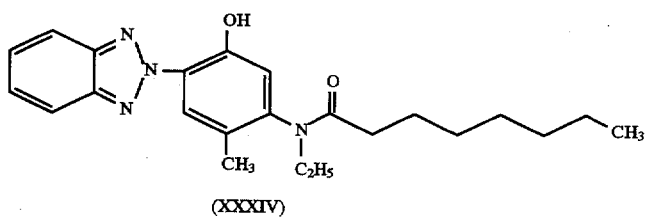

(XXXIV)

It is obtained as a liquid compound. Its ¹H-NMR spectrum in CDCl₃ (with tetramethylsilane as internal reference) showed peaks at δ 11.5 (s, 1H, phenolic OH), 8.35 (s, 1H, atom), 7.95 (m, 2H, arom), 7.5 (m, 2H, arom), 6.97 (s, 1H, arom), 4.1 (m, 1H, one proton of NCH₂—CH₃), 3.3 (m, 1H, one proton of NCH₂—CH₃), 2.25 (s, 3H, CH₃—Ar), 2.08 (m, 1H, one proton of N—CO—CH₂—), 1.98 (m, 1H, one proton of N—CO—CH₂—), 1.6 (m, 2H, CH₂ in the octyl chain), 1.2 (tall and sharp multiplet, 11H, methyl of N-ethyl group and 8 protons 2×4 CH₂'s in the octyl chain), and 0.8 (t, 3H, CH₂—CH₃ of n-octyl group). Its retention time in HPLC was 21.65 min, was 99.5% pure by peak area percent. Its UV-Vis (in MeOH) showed $\lambda_{max}$ 336 ran, half-bandwidth 78 nm, and $\epsilon_{max}$ 1.91×10⁴. Its elemental percent composition was calculated for $C_{23}H_{30}N_4O_2$ (M.W. 394.5): Calculated: C, 70.02; H, 7.66; N, 14.20; Found: C, 69.81; H, 7.50; N, 14.19.

showed peaks at δ 10.98 (s, 1H, phenolic OH), 8.3 (s, 1H, arom), 7.92 (s, 1H, arom), 7.9 (d, 1H, arom), 7.45 (d, 1H, arom), 6.95 (s, 1H, arom), 4.10 (m, 1H, one proton of N CH₂—CH₃), 3.3 (m, 1H, one proton of NCH₂—CH₃), 2.25 (s, 3H, CH₃—Ar), 2.05 (m, 1H, one proton of N—CO—CH₂—), 1.90 (m, 1H, one proton of N—CO—CH₂—), 1.58 (m, 8H, 4×CH₂'s), 1.13 (merged multiplet, 3H, NCH₂CH₃), and 0.8 (t, 3H, CH₂—CH₃ of n-octyl group). Its retention time in HPLC was 22.35 min, was 98.5% pure by peak area percent. Its UV-Vis (in MeOH) showed $\lambda_{max}$ 342 nm, half-bandwidth 80 nm, and $\epsilon_{max}$ 2.0×10⁴. Its elemental percent composition was calculated for $C_{23}H_{29}Cl_1N_4O_2$ (M.W. 428.9): Calculated: C, 64.40; H, 6.81; N, 13.06; Cl, 8.26 Found: C, 64.30; H, 6.71; N, 12.88; Cl, 8.36.

EXAMPLE 21

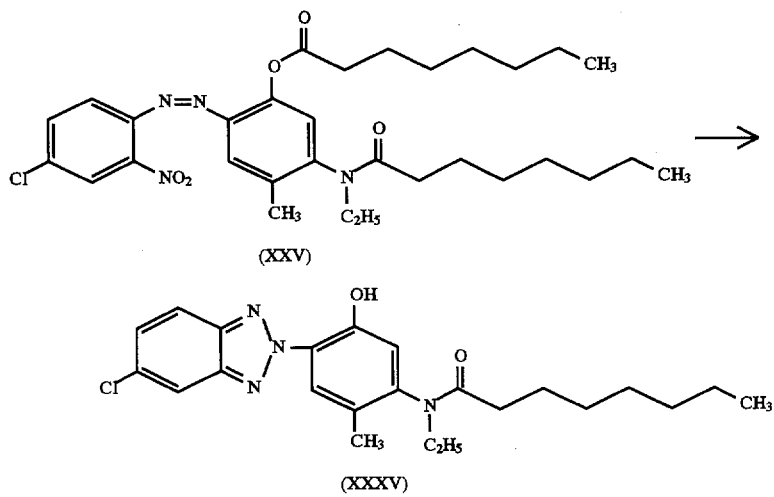

It is obtained as a liquid compound. Its ¹H-NMR spectrum in CDCl₃ (with tetramethylsilane as internal reference)

EXAMPLE 22

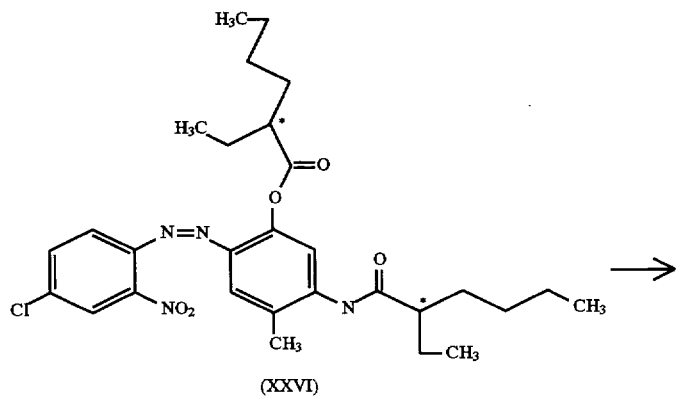

-continued

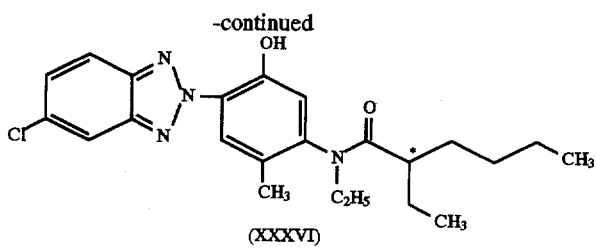

(XXXVI)

It is obtained as a liquid compound. Its $^1$H-NMR spectrum in CDCl$_3$ (with tetramethylsilane as internal reference) showed peaks at δ 10.94 (s, 1H, phenolic OH), 8.3 (s, 1H, arom), 7.9 (s, 1H, arom), 7.86 (d, 1H, arom), 7.45 (d, 1H, arom), 6.98 (s, 1H, arom), 4.20 (m, 1H, one proton of N CH$_2$—CH$_3$), 3.18 (m, 1H, one proton of NCH$_2$—CH$_3$), 2.25 (s, 3H, CH$_3$—Ar), 2.03 (m, 1H, methine), 1.58 (m, 2H, CH$_2$), 1.38 (m, 2H, CH$_2$), 1.18 (m, 7H, 2×CH$_2$'s, merged with triplet of methyl protons in N-ethyl group), and 0.82 (m, 6H, 2×CH$_3$'s). Its retention time in HPLC was 21.93 min, was 98% pure by peak area percent. Its W-Vis (in MeOH) showed $\lambda_{max}$ 342 nm, half-bandwidth 80 nm, and $\epsilon_{max}$ 2.0×10$^4$. Its elemental percent composition was calculated for C$_{23}$H$_{29}$Cl$_1$N$_4$O$_2$ (M.W. 428.9): Calculated: C, 64.40; H, 6.81; N, 13.06; Cl, 8.26 Found: C, 64.66; H, 6.80; N, 12.66; Cl, 8.43.

Examples 17 through 22 again clearly illustrate selective O-deacylation during the reductive ring closure step while leaving the tert-amido group intact.

The invention has been described in detail with particular reference to preferred embodiments, but it will be understood that variations and modifications can be effected within the spirit and scope of the invention.

We claim:

1. A method for preparing a compound of formula (III):

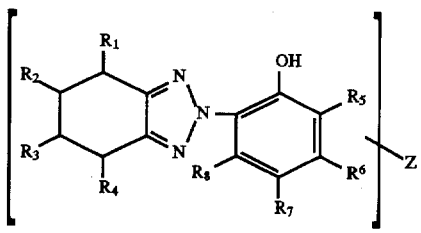

(III)

wherein:

R$_1$, R$_2$, R$_3$, R$_4$, R$_5$, R$_6$, R$_7$ and R$_8$ are independently: H; halogen; cyano; —CO$_2$Y where Y is H or an alkyl group or aryl group; carbamoyl group; sulfoxido group; sulfonyl group; sulfonato group; sulfonamido group; alkyl group; alkoxy group; aryl group; heteroaryl group; aryloxy group; or any two or more of adjacent ones of R$_1$ through R$_4$, or R$_5$ through R$_7$ may together form an alicyclic group, or complete, together with the carbon atoms of the benzene ring to which they are attached, an aromatic group or heteroaryl group; or Z, with the proviso that at least one of R$_1$ through R$_8$ is Z; or R$_8$ is OH; where Z is a group of the formula:

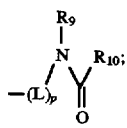

where L is a linking group; R$_9$ and R$_{10}$ are independently: a branched or unbranched alkyl or perfluoro alkyl group which may contain one or more hetero atoms and may be substituted with one or more hydroxyl groups, and p is 0 or 1;

said process comprising ring closure of an azo dye compound of formula (IV):

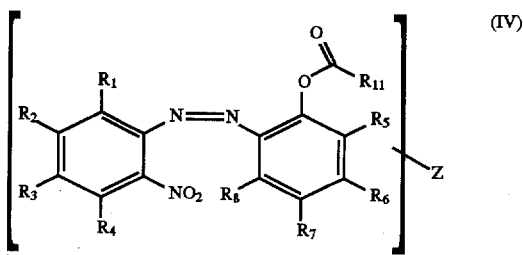

(IV)

whereby the ester group —OCOR$_{11}$ is removed during the ring closure step liberating the free phenolic group, where R$_{11}$ is a branched or unbranched alkyl or perfluoro alkyl group which may contain one or more hetero atoms and may be substituted with one or more hydroxyl groups, and may be the same as or different from R$_{10}$.

2. A method according to claim 1, wherein said ring closure is a noble metal catalyzed hydrogenation or a non-catalytic reductive ring closure of the azo dye of formula (IV).

3. A method according to claim 2 wherein the group R$_{10}$ represents a 1–12 carbon atom substituted or unsubstituted alkyl group.

4. A method according to claim 1 wherein R$_{10}$ is selected from: 1–18 carbon atom alkyl groups with or without 1 to 6 intervening oxygen, sulfur or nitrogen atoms; benzyl group; tetrahydropyranyl group; and 3 to 20 carbon atom trialkyl silyl group.

5. A method according to claim 1 wherein R$_{10}$ is selected from: methyl; ethyl; n-propyl; isopropyl; butyl; pentyl; t-butyl; t-amyl; methoxymethyl; methoxyethoxymethyl; and 3 to 20 carbon atom trialkyl silyl group; phenyl group; pyridinyl; imidazolyl; pyrrolyl; furyl; and thienyl.

6. A method according to claim 9 wherein R$_8$ is H or OH.

7. A method according to claim 1, wherein the method comprises reacting the compound of formula (IV) with an appropriate reducing agent selected from hydrogen, thiourea-S,S-dioxides and dithionite salts.

8. A method according to claim 7 wherein the reducing agent selected from thiourea-S,S-dioxide and dithionite salts in a basic aqueous solution.

9. A method according to claim 8 wherein the aqueous solution is an alcoholic solution.

10. A method according to claim 9 wherein the temperature is maintained at 60° to 80° C. and the reducing agent is thiourea-S,S-dioxide.

11. A method according to claim 10 wherein the ring closure step is performed for 2 to 3 hours.

12. A method according to claim 1 wherein the ring closure step comprises the catalytic hydrogenation of the protected formula (IV) compound.

13. A method according to claim 12 wherein the catalyst is a noble metal catalyst.

14. A method according to claim 13, wherein the noble metal catalyst is a palladium-charcoal catalyst.

* * * * *